United States Patent [19]

Lenthe et al.

[11] 4,176,133
[45] Nov. 27, 1979

[54] PROCESS FOR ISOLATING N,N-DIMETHYLAMINOACETONITRILE FROM WATER MIXTURES

[75] Inventors: Manfred Lenthe, Odenthal; Gerhard Dankert, Cologne, both of Fed. Rep. of Germany

[73] Assignee: Bayer Aktiengesellschaft, Leverkusen, Fed. Rep. of Germany

[21] Appl. No.: 953,048

[22] Filed: Oct. 19, 1978

[30] Foreign Application Priority Data

Nov. 2, 1977 [DE] Fed. Rep. of Germany ....... 2748964

[51] Int. Cl.² .......................................... C07C 121/43
[52] U.S. Cl. ............................................. 260/465.5 R
[58] Field of Search ................... 260/465.5 R, 465.5 A

[56] References Cited

U.S. PATENT DOCUMENTS

| 4,011,254 | 3/1977 | Kobayashi et al. | 260/465.5 R |
| 4,022,815 | 5/1977 | Schlecht et al. | 260/465.5 A |
| 4,113,764 | 9/1978 | Distler et al. | 260/465.5 A |

OTHER PUBLICATIONS

Turner, J.A.C.S., 68 (1946), pp. 1607–1608.
Luten, C.A., 33 (1939), 4584.
Yashunskii, C.A., 59 (1963), 602–f.

*Primary Examiner*—Joseph P. Brust
*Attorney, Agent, or Firm*—Sprung, Felfe, Horn, Lynch & Kramer

[57] ABSTRACT

In the recovery of N,N-dimethylaminoacetonitrile from a mixture thereof with water by extraction with an organic solvent thereby to form an aqueous phase and an organic solvent phase containing the nitrile, separating the organic phase, and recovering the nitrile from the organic solvent, the improvement which comprises employing 1,2-dichlorobenzene as the organic solvent. Recovery of the nitrile from the organic solvent can be accomplished by distilling of the nitrile, the undistilled solvent being recycled for further use.

7 Claims, 1 Drawing Figure

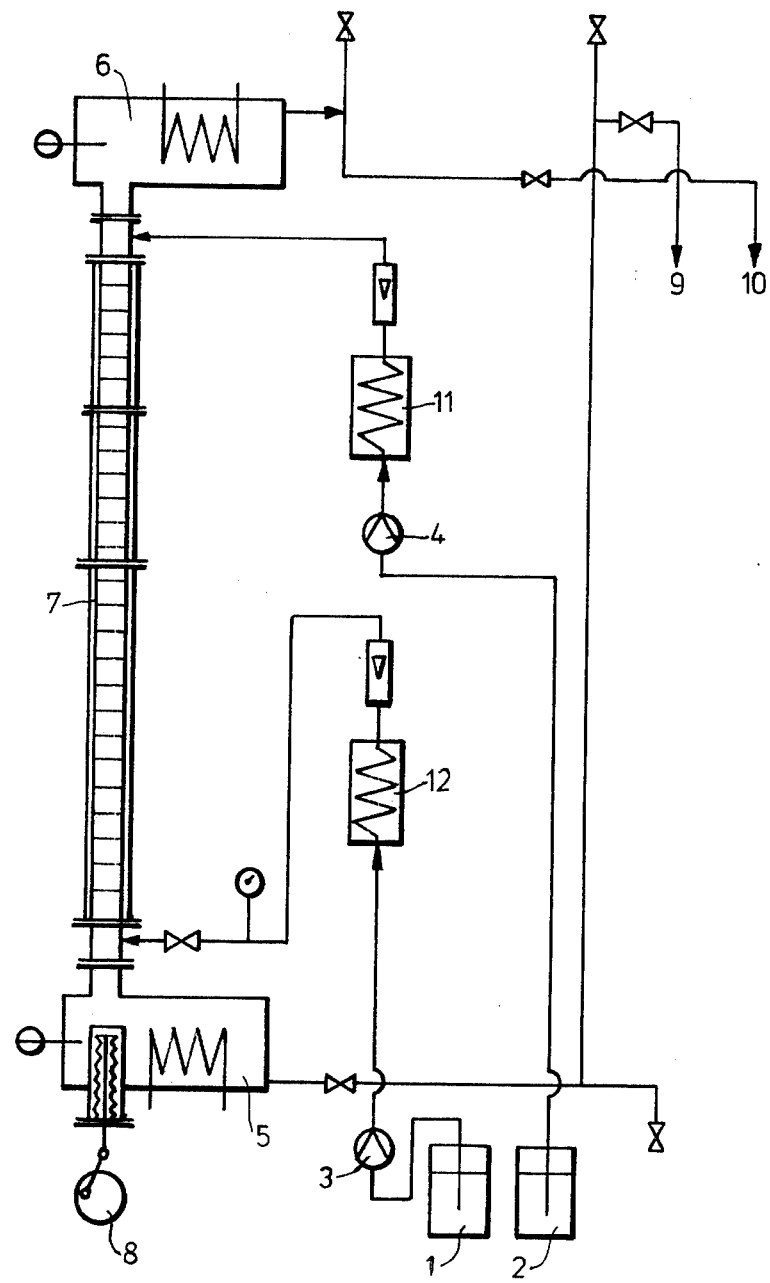

PROCESS FOR ISOLATING N,N-DIMETHYLAMINOACETONITRILE FROM WATER MIXTURES

The invention relates to an unobvious process for isolating N,N-dimethylaminoacetonitrile, by extraction with 1,2-dichlorobenzene, from the nitrile/water mixtures obtained during the preparation from dimethylamine, hydrocyanic acid and formaldehyde.

The preparation of N,N-dimethylaminoacetonitrile from dimethylamine, hydrocyanic acid and formaldehyde by a reaction which has been known for a long time (the so-called "Mannich reaction" type; see "Organikum", VEB Deutscher Verlag der Wissenschaften, Berlin, 8th edition (1968), page 447 et seq.) takes place in high yields. However, it is difficult to separate off water from the product mixture. Pure N,N-dimethylaminoacetonitrile has a boiling point of 137° C./760 mmHg and, in the pressure range suitable for industrial distillation, forms azeotropic mixtures with water which contain in each case about 50% by weight of the two components. For this reason, in order to isolate the nitrile, extraction with chloroform or benzene has been proposed (a process according to R. A. Turner, J. Am. Chem., Soc. 68, 1,607 (1946)), and extraction with diethyl ether has been recommended by other authors (Eschweiler, Liebigs Ann. Chem. 279, 43 (1894)).

The extraction agents mentioned have the disadvantage of either high toxicity (chloroform and benzene) or low flash points (benzene and ether); they all have lower boiling points than the product to be isolated and must therefore be distilled out of the extraction mixtures, with a high consumption of energy.

It has now been found that N,N-dimethylaminoacetonitrile is obtained in a particularly simple manner when an N,N-dimethylaminoacetonitrile/water mixture, such as that obtained from dimethylamine, hydrocyanic acid and formaldehyde, is extracted with 1,2-dichlorobenzene.

It is surprising that 1,2-dichlorobenzene avoids the disadvantages of the extraction agents known according to the state of the art and thus represents a solvent which is superior in practice. As has also been found, when 1,2-dichlorobenzene is used, the separation of the entrained water from the extract phase, which is necessary in most cases, can be easily effected by subsequent distillation at low temperatures. The process according to the invention thus involves a technical advance.

The extraction of dimethylaminoacetonitrile by the extraction process according to the invention can give high yields when it is carried out at temperatures of about 5° to 90° C., preferably about 15° to 30° C., and when about 1.5 to 10 parts by weight, preferably about 2.5 to 5 parts by weight, of 1,2-dichlorobenzene are employed per part by weight of the N,N-dimethylaminoacetonitrile/water mixture.

The nitrile/water mixture employed can contain salts, for example because of the use of sodium cyanide in the reaction for the formation of the nitrile; it can also be salt-free if the reaction is carried out with hydrogen cyanide.

The invention is further described with reference to the accompanying drawing which is a flow sheet of the process.

In the drawing a mixture of N,N-diemthylaminoacetonitrile and water is introduced from the reservoir for the water/nitrile mixture (1) and 1,2-dichlorobenzene from the reservoir (2) via the pumps (3) and (4) and the heat exchangers (12) and (11), respectively, into the lower and, respectively, upper part of a pulsating (8) perforated tray extraction column (7), via rings of nozzles.

The disperse organic phase which forms in the continuous aqueous phase flows through the column and is continuously redistributed on the plates by a stroke of the bellows in the sump (5) and finally flows out via the overflow (9). The aqueous phase passes through the column from the bottom upwards (countercurrent) and exits at (10) via the head (6).

The process is, in general, composed of an extraction, which can be carried out in an installation such as that shown in the accompanying drawing, and a subsequent distillation. During the extraction, an aqueous phase (consisting virtually only of water) and an organic phase are obtained; the latter consists mainly of the solvent (1,2-dichlorobenzene) and the desired nitrile and small amounts of water. This organic phase is fractionated in the subsequent distillation.

The recycling of the 1,2-dichlorobenzene recovered in the subsequent distillations into the extraction, such as is necessary for the profitability of a process, has only a very slight influence on the quality of the extraction and can be carried out with very low discharge rates, so that there are scarcely any losses in chemicals.

If the distillation of the organic phase obtained in the extraction is carried out in the pressure range from about 1 to 760 mm Hg, preferably about 10 to 200 mm Hg, relatively small amounts of water, which generally contain about 20 to 80 per cent by weight of nitrile, also pass over and the proportion of 1,2-dichlorobenzene in this fraction is very low. The fraction which consists mainly of water and nitrile is added again to the starting mixture which is introduced into the extraction column.

The N,N-dimethylaminoacetonitrile thus isolated according to the invention and the α-aminocarboxylic acid to be obtained therefrom by saponification are important intermediates in the preparation of dyestuffs, textile auxiliaries, pharmaceutical products and active compounds for plant protection. Thus, for example, tetrachloroethylenebis-isocyanide dichloride can be obtained from the abovementioned nitrile in a rearrangement reaction by reaction with chlorine:

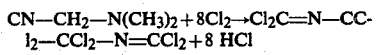

$$CN-CH_2-N(CH_3)_2 + 8Cl_2 \rightarrow Cl_2C=N-CCl_2-CCl_2-N=CCl_2 + 8 HCl$$

With hydrogen fluoride, the product gives N,N'-bis-(trifluoromethyl)-tetrafluoroethylenediamine, and perfluoro-2,5-diazahexa-2,4-diene (obtained by another route and described by P. H. Ogden and R. A. Mitsch, J. Ann. Chem. Soc. 89, 5,008 (1967)) is obtained from the latter by reaction with sodium fluoride, 2 moles of hydrogen fluoride being split off. This perfluoro compound gives, in a cyclization reaction with N-methyl-N'-(4-chlorophenyl)-thiourea, the plant protection fungicide 2-methylimino-3-(4'-chlorophenyl)4,5-bis-(trifluoromethylimino)-thiazolidine, which has the formula

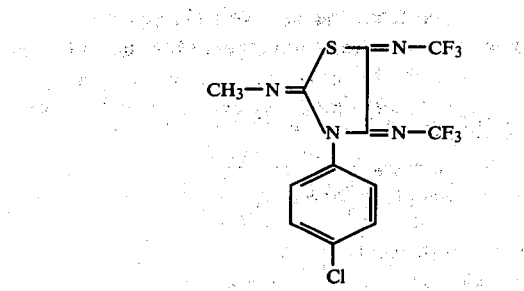

and which is known from the literature (see DT-OS (German Published Specification) 2,062,438 and U.S. Pat. Spec. No. 3,895,020.

The process of the present invention is illustrated by the following examples:

EXAMPLE 1

Dimethylamine, formaldehyde and hydrocyanic acid is reacted yielding a mixture containing 48 percent by weight of N,N-dimethylaminoacetonitrile and water. The extraction of this mixture with 1,2-dichlorobenzene is effected as follows:

In the installation shown 2.9 kg/hour of the mixture with a content of 48% by weight of N,N-dimethylaminoacetonitrile and 10 kg/hour of 1,2-dichlorobenzene were introduced at 24° C.

The bellows in the sump (3) were stroked 20 mm at a pulsation frequency of 200/minute. After a steady state had been established, the aqueous phase had a content (according to gas chromatography) of 99.9% by weight of water (dimethylaminoacetonitrile could no longer be detected) and the organic phase contained 87.5% by weight of 1,2-dichlorobenzene and 12.3% of nitrile as well as small amounts of water.

228.2 kg of the organic phase were distilled over a 3 m packed column under 100 mbars (about 75 mm Hg) and at a reflux ratio of 5:1. After a first running of 2.4 kg with a water content of 17.3%, 81.1% of nitrile and a small proportion of o-dichlorobenzene, which passed over at 50° C., was collected at 69° C. as a main fraction of 21.4 kg, which had a content of 99.9% by weight of N,N-dimethylaminoacetonitrile. In addition to dichlorobenzene, the sump product of 204.4 kg also contained 0.1% of nitrile.

EXAMPLE 2

2.9 kg/hour of aqueous phase containing 48% of nitrile and 10 kg/hour of o-dichlorobenzene were put through the installation described in Example 1 at 80° C. and with a pulsation stroke of 10 mm at a frequency of 132/minute. The raffinate flowing out contained 99.7% of water and 0.3% of nitrile and the extract had contents of 11.1% by weight of nitrile and 85.9% of 1,2-dichlorobenzene as well as 3% of water, most of which was present in a second phase. Distillation of 170 kg of the extract under the conditions described in Example 1 gave a first running of 12.5 kg, containing 41.5% by weight of water, 55.1% by weight of nitrile and 3.4% of dichlorobenzene, and a main running at 69° C. of 12.2 kg, containing 99.9% of nitrile. No further nitrile could be detected by gas chromatography in the sump product of 144.9 kg.

EXAMPLE 3

8.4 kg of 1,2-dichlorobenzene and 4.5 kg of a mixture containing 45% of nitrile and 55% of water were introduced per hour into the installation described in Example 1 at 23.5° C. and under the same extraction conditions as in Example 2. The aqueous phase flowing out via the head still had a nitrile content of 2.1% by weight, and the collected extract phase contained 23.4% by weight of nitrile, 76.1% by weight of dichlorobenzene and 0.5% of water.

In the distillation of 98.2 kg of extract as in Example 1, 2.1 kg of a first running, containing 23.4% by weight of water, 75.2% by weight of nitrile and a small proportion of dichlorobenzene, and a main fraction of 23 kg of pure nitrile were obtained. In addition to dichlorobenzene, the sump product of 73 kg which remained contained a trace of N,N-dimethylaminoacetonitrile.

EXAMPLE 4

2.9 liters of the nitrile/water mixture described in Example 2, with a content of 10% by weight of sodium chloride, were extracted per hour with 10 kg of a mixture of 99.9% by weight of 1,2-dichlorobenzene and 0.1% by weight of dimethylaminoacetonitrile in the installation described in Example 1 at 23.5° C. and under the conditions of Example 2. The aqueous phase which flowed out contained 0.2% by weight of nitrile, and the extract had contents of 88% by weight of 1,2-dichlorobenzene and 12% by weight of nitrile. Only traces of water were present.

Distillation of 205 kg of the extract under the conditions of Example 1 gave, after a first running of 1 kg with a nitrile content of 74.8%, 10.3% of water and 14.9% of 1,2-dichlorobenzene, a main fraction of 23.8 kg containing 99.9% of nitrile. The sump product of 180 kg had a nitrile content of less than 0.1%.

It will be appreciated that the instant specification and examples are set forth by way of illustration and not limitation, and that various modifications and changes may be made without departing from the spirit and scope of the present invention.

What is claimed is:

1. In the recovery of N,N-dimethylaminoacetonitrile from a mixture thereof with water by extraction with an organic solvent thereby to form an aqueous phase and an organic solvent phase containing the nitrile, separating the organic phase, and recovering the nitrile from the organic solvent, the improvement which comprises effecting the extraction at about 5° to 90° C. with about 1.5 to 10 parts by weight of 1,2-dichlorobenzene per part by weight of the water/nitrile mixture.

2. A process according to claim 1, in which the extraction is carried out at a temperature from about 15° to 30° C.

3. A process according to claim 1, in which about 2.5 to 5 parts by weight of 1,2-dichlorobenzene are employed per part by weight of the water/nitrile mixture.

4. A process according to claim 1, in which after the separation from the aqueous phase the 1,2-dichlorobenzene phase is fractionally distilled to distill off the nitrile.

5. A process according to claim 4, in which the distillation is carried out at a pressure of about 1 to 760 mm Hg.

6. A process according to claim 4, in which the distillation is carried out at a pressure of about 10 to 200 mm Hg.

7. A process according to claim 6, in which the extraction is carried out at a temperature from about 15° to 30° C. and about 2.5 to 5 parts by weight of 1,2-dichlorobenzene are employed per part by weight of the water/nitrile mixture.

* * * * *